US00PP13234P3

(12) United States Plant Patent
Michalik

(10) Patent No.: US PP13,234 P3
(45) Date of Patent: Nov. 12, 2002

(54) VARIETY OF GERANIUM PLANT NAMED 'PACTWO'

(75) Inventor: Andrea Michalik, Dresden (DE)

(73) Assignee: Elsner pac Jungpflanzen (DE)

( * ) Notice: Subject to any disclaimer, the term of this patent is extended or adjusted under 35 U.S.C. 154(b) by 0 days.

(21) Appl. No.: 09/739,022

(22) Filed: Dec. 8, 2000

(65) Prior Publication Data

US 2002/0073464 P1 Jun. 13, 2002

(51) Int. Cl.[7] ..... A01H 5/00

(52) U.S. Cl. ..... Plt./329

(58) Field of Search ..... Plt./329, 325, 324

*Primary Examiner*—Kent L. Bell

(74) *Attorney, Agent, or Firm*—Webb Ziesenheim Logsdon Orkin & Hanson, P.C.

(57) ABSTRACT

A new and distinct pelargonium plant with exciting red-purple colored flowers above medium green foliage. The plant is suitable for pot planting and as a bedding plant.

1 Drawing Sheet

BOTANICAL/COMMERCIAL CLASSIFICATION

*Pelargonium×hortorum*; Zonal Geranium.

VARIETAL DENOMINATION

'Pactwo'.

BACKGROUND OF THE INVENTION

The present invention comprises a new and distinct cultivar of *Pelargonium×hortorum* known by the varietal name 'Pactwo'. The new variety was discovered in 2000 in a selective breeding program in Dresden, Germany. The new variety was a naturally occurring branch mutation discovered on a plant of the unpatented variety 'Penbalu' (PEL 1416). The new variety exhibits the growth and flower color of its parent, but differs in its earlier flowering and improved resistance to heat. The new variety was first asexually reproduced by cuttings in Dresden, Germany in 2000. The new variety has been trial and field tested at Connellsville and has been found to retain its distinctive characteristics and remain true to type through successive propagations. The new variety is earlier in flowering, more heat resistant, and has more intense flower color than its parental cultivar, 'Penbalu'.

DESCRIPTION OF THE DRAWING

The accompanying photographic drawing illustrates the new variety, with the color being as nearly true as is possible with color illustrations of this type.

DESCRIPTION OF THE PLANT

The following detailed description sets forth the characteristics of the new cultivar. The data which defines these characteristics were collected by asexual reproductions carried out in Dresden, Germany. Observations were made when the plants were 9 months old, grown in 19 cm diameter containers. The color readings were taken outdoors in shadow during summer. Color references are primarily to The R.H.S. Colour Chart of The Royal Horticultural Society of London.

PLANT

Form: Erect.
Height from media surface to top of foliage: 35–40 cm.
Height from media surface to top of umbel: 50 cm.
Width (spread): 40 cm.
Growth: Good branching.
Strength: Does not require artificial support.
Response time: 3.5 weeks.
Leaves:
- *Size.*—8–10 cm.
- *Shape.*—Cordate.
- *Margin.*—Entire.
- *Base.*—Cordate.
- *Texture.*—Velvety.
- *Color.*—Upper surface: 137A with a 200D zone. Lower surface: 137D.
- *Ribs and veins.*—Color: 138B.

Petioles:
- *Color.*—138B.
- *Length.*—4–6 cm.
- *Diameter.*—4 mm.

Stem/branches:
- *Color.*—138B.
- *Stem length.*—30–35 cm.
- *Branch length.*—20–25 cm.
- *Internode length.*—3–4 cm.

THE BUD

Shape when just showing color:
- *Overall.*—Spherical.
- *Individual bud.*—Spherical.

Color: Yellow-Green Group 144A.
Size when just showing color:
- *Umbel.*—10–12 cm across.
- *Individual bud.*—1.3–1.5 cm long; 1.0 cm wide.

INFLORESCENCE

Quantity per plant: 40–70 per season.
Blooming habit: Semi-double; flowers during frost free season.

Size of fully open bloom: 4.5 cm across.
Borne: Umbel; flowers on pedicel; pedicel on peduncle.
Flowers:
*Form.*—Zygomorph.
*Number of petals.*—7–9.
*Size.*—2.0–2.5 cm across.
*Petals.*—Margin: Entire. Petal shape: Round. Length: 2.0–2.5 cm. Width: 2.0–2.5 cm. Apex: Round. Base: Pointed. Color: Upper surface: Red-Purple Group 57A. Lower surface: Red-Purple Group 57A.
*Texture and appearance.*—Velvety.
Petaloids:
*Quantity.*—3.
*Shape.*—Irregular.
*Color: Upper surface: Red-Purple Group* 57A. Lower surface: Red-Purple Group 57A.
Sepals:
*Quantity.*—5.
*Margin.*—Entire.
*Shape.*—Lanceolate.
*Length.*—0.7 cm.
*Width.*—0.4 cm.
*Apex.*—Pointed.
*Base.*—Wide.
*Color.*—About 138C (Both surfaces).
Pedicel:
*Length.*—2.5–3.0 cm.
*Color.*—138C.
Peduncle:
*Length.*—9–11.0 cm.
*Color.*—138B.
Disease/pest resistance: No susceptibility to diseases or pests has been noted to date.
Lasting quality: Long-lasting; 4 weeks per umbel.

REPRODUCTIVE ORGANS

Stamens:
*Anthers.*—3 mm long.
*Filaments.*—Length: 0.5 cm maximum. Color: Pink. Pollen: Yellow.
Pistils:
*Number.*—One, five parted.
*Length.*—0.3–0.4 cm.
*Stigma.*—Red.
*Style.*—0.8 cm.
Ovaries:
*Color.*—Greenish.
*Length.*—0.4 cm.
Fruit:
*Occurrence.*—Rare.
*Shape.*—Oval.
*Length.*—4 mm.
*Width.*—1.5 mm.
*Color.*—165A.

GENERAL CHARACTERISTICS

1. Suitable for pot and as bedding plants.
2. Prominent zoning present.
3. Red-purple flower color.
4. Heat resistant.

I claim:

1. A new and distinct variety of geranium plant substantially as shown and described.

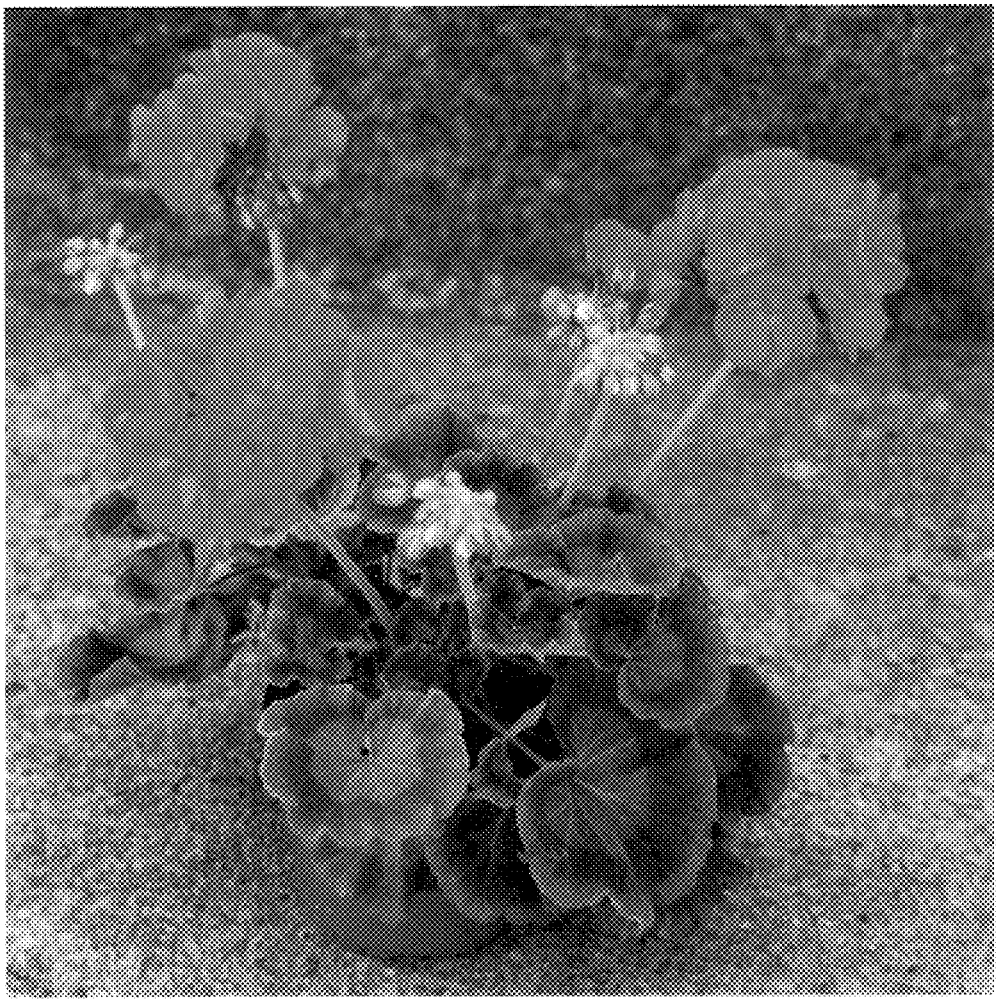

* * * * *